United States Patent [19]

McKee et al.

[11] 4,348,358

[45] Sep. 7, 1982

[54] COLORIMETRIC DOSIMETER

[75] Inventors: Elmer S. McKee; Paul W. McConnaughey, both of Pittsburgh, Pa.

[73] Assignee: Mine Safety Appliances Company, Pittsburgh, Pa.

[21] Appl. No.: 190,593

[22] Filed: Sep. 25, 1980

[51] Int. Cl.³ .............................................. G01N 21/78
[52] U.S. Cl. .................................. 422/56; 23/232 R; 422/58; 422/87
[58] Field of Search .................. 422/56, 57, 58, 59, 422/60, 86, 87, 88; 23/232 R

[56] References Cited

U.S. PATENT DOCUMENTS

| | | | |
|---|---|---|---|
| 2,606,102 | 8/1952 | Cook | 422/56 |
| 2,895,807 | 7/1959 | Sorg et al. | 23/232 R X |
| 3,378,348 | 4/1968 | McConnaughey | 422/60 |
| 3,620,677 | 11/1971 | Morison | 422/56 |
| 3,701,633 | 10/1972 | Davis | 422/58 |
| 3,884,641 | 5/1975 | Kraffczyk et al. | 422/87 X |
| 3,985,017 | 10/1976 | Goldsmith | 23/232 R X |
| 4,145,186 | 3/1979 | Andersen | 422/86 X |
| 4,159,304 | 6/1979 | Shono | 422/59 X |
| 4,235,097 | 11/1980 | Kring et al. | 422/88 X |
| 4,269,804 | 5/1981 | Kring | 422/86 |

FOREIGN PATENT DOCUMENTS 1498909 4/1969 Fed. Rep. of Germany .... 23/232 R

Primary Examiner—Arnold Turk

[57] ABSTRACT

A gas dosimeter comprises a strip substrate coated or impregnated with a color-changing reagent; the strip is disposed lengthwise in a transparent tube, one end of which is openable and is spaced by a diffusion path from one end of the strip. When the dosimeter tube is opened and exposed to the atmosphere containing detectable gas, a color change develops lengthwise of the strip dependent on the dosage exposure to the gas.

12 Claims, 1 Drawing Figure

U.S. Patent
Sep. 7, 1982
4,348,358
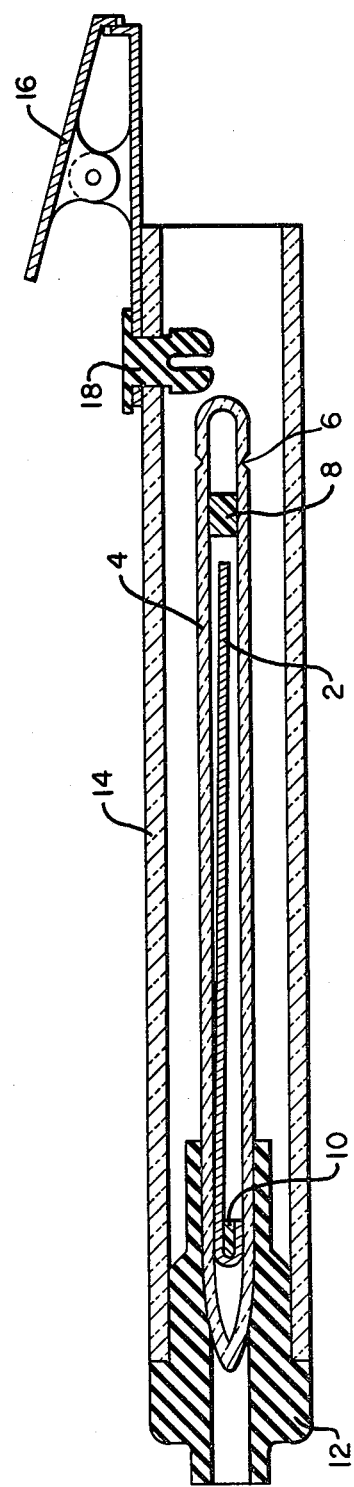

COLORIMETRIC DOSIMETER

FIELD OF THE INVENTION

This invention relates to colorimetric dosimeters of the length-of-stain type for determining the dosage exposure to noxious gases in the atmosphere.

BACKGROUND OF THE INVENTION

In colorimetric gas dosimeters a color-changing reagent is exposed to ambient air, usually through a diffusion path to minimize convection current errors, and the amount of color development is a measure of the dosage exposure to the detected gas. Dosage exposure is the integral over a time period of the concentration x time product. The "8-hour time weighted average" exposures to toxic gases, proscribed by OSHA as permissible exposure limits, is the dosage exposure over an 8-hour period divided by 8.

Two types of colorimetric gas dosimeters have heretofore been used. The length-of-stain type has an elongate bed of indicating chemical, usually with an active component on an inert granular carrier, disposed in a glass tube. Gas to be detected diffuses from an open end of the tube to and through the bed; a color change develops lengthwise of the bed, the length-of-stain being a measure of the dosage exposure. Such tubes have been widely used for measuring CO dosage. However, for many gases, and as exposure criteria are tightened, conventional length of stain tubes are not sufficiently sensitive to measure small doses. The length-of-stain developed for a given dosage is proportional to the amount of active component, but when the amount of active chemical is decreased to increase sensitivity, the intensity of the developed color also diminishes making it difficult to see the stain.

The color comparison type of dosimeter conventionally exposes an entire major surface of a reagent impregnated paper or similar substrate to the atmosphere. The exposure causes a spectrum of color change or variations depending on the dosage exposure. The exposed paper is compared to one or more color standards in order to read out the dosage exposure. Color comparison methods suffer inaccuracies because of wide individual subjective differences in comparing colors.

SUMMARY OF THE INVENTION

It is an object of this invention to provide a length-of-stain gas dosimeter of improved sensitivity that is easy to read. Other objects and advantages will be apparent from the description and claims.

The gas dosimeter of this invention comprises a detecting strip substrate coated or impregnated with a color-changing reagent responsive to a gas being determined; the strip is disposed lengthwise in a transparent tube, one end of which is openable and is spaced by a diffusion path from one end of the strip. When the dosimeter tube is opened and exposed to the atmosphere containing detectable gas, a color change develops lengthwise of the strip dependent on the dosage exposure to the gas. The diffusion path may be an open length of tube, but preferrably includes a porous diffusion barrier, such as a plug of open cell foamed synthetic resin. The dosimeter tube may be housed within a larger unbreakable protective tube.

BRIEF DESCRIPTION OF THE DRAWING

The accompanying drawing is a cross-sectional view of a dosimeter according to the invention.

DESCRIPTION OF THE PREFERRED EMBODIMENT

Referring to the drawing, a gas dosimeter tube consists of a detecting strip 2 positioned lengthwise in transparent tube 4, which is sealed at both ends and has a score line 6, near one end. A small plug of open cell foam 8, or other porous barrier such as a wad of cloth or fibers, or a porous membrane, is positioned between the end of the strip and the score line. The detecting strip is held in position by folding one end around a partially compressed resilient plug 10 such that one side of the strip is spaced apart from said tube a substantial portion of the length of the strip.

The dosimeter tube may be made of any transparent material inert to the gas being determined, but is usually glass. The glass tube is protected by a second larger transparent tube 14 of unbreakable plastic which is provided with a clip 16, secured by grommet 18, for attachment to a lapel or other clothing of the wearer. A grommet 12 of rubber or other resilient material has an axial aperture to releasibly engage and support the dosimeter tube. The outer surface of the grommet is releasibly engaged by the protective tube 14, providing a simple, inexpensive, convenient and practical dosimeter assembly.

When the dosimeter is to be used the grommet and dosimeter tube are pulled out of the protective tube, the end of the dosimeter tube is broken off at the score line, and the grommet and dosimeter tube are reinserted into the protective tube. Exposure of the detecting strip to the atmosphere through the diffusion path results in a stain developing lengthwise of the strip; the length of the stain is dependent on and is a measure of the dosage exposure. The length of stain development for a given dosage can be adjusted by varying the amount of reagent on the strip, the size of the strip, the tube size, the distance from the end of the strip to the open end of the tube and the nature and size of the diffusion path. For the purpose of measuring dosages over 8-hour shifts, tubes having an inside diameter between about 2 mm and 6 mm are generally used. When the monitoring period is over, e.g. an 8-hour work shift, the dosimeter tube is removed and length of the developed stain is measured. If desired a printed scale can be inserted in the protective tube for measuring the stain length.

The detector strip is a substrate carrying a reagent that changes color on contact with a gas to be determined. The substrate is preferably a filter paper, but other porous substrates, e.g., blotting paper, felts, cloths or wicks, or non-porous substrates, for example glass rods or plastic strips, may be used. The reagent can be carried on only a portion of the substrate as, for example, with a narrow lengthwise line of reagent carried on a wide substrate. The substrate is selected to be inert to the reagent and the gas being determined. The substrate is saturated or coated with a solution of reagent in water, alcohol or other volatile solvent and then dried, leaving porous substrates impregnated with reagent and non-porous substrates coated with reagent. In some cases it is desirable to include a humectant impregnant to accelerate the colorimetric reaction; in such cases a humectant of low volatility, such as glycerine, for example, can be incorporated in the reagent solution. In appropriate cases, very uniform reagent distribution is obtained by forming the reagent in situ in a porous substrate by reaction of two or more solutions.

EXAMPLE 1

A sheet of Whatman #1 filter paper is saturated with a 3% silver nitrate solution in deionized water and laid over a second sheet of filter paper saturated with a ½% sodium cyanide solution in deionized water. The sodium cyanide solution diffuses up through the first sheet for a period of about five minutes, reacting with the silver nitrate forming a silver cyanide precipitate uniformly impregnating the filter paper. The sheet containing precipitated silver cyanide is carefully lifted from the other paper, dried at room temperature or in an oven at up to 90° C., and then cut into strips.

A strip of the white impregnated paper 2.5 mm wide and 80 mm long was incorporated in a dosimeter tube of the drawing. The dosimeter tube had a 5 mm inside diameter and the end of the detecting strip was spaced 10 mm from the score line. When the tube was opened and exposed to an atmosphere containing 10 ppm $H_2S$, a brownish-black stain developed as follows:

| TIME OF EXPOSURE (hours) | STAIN LENGTH (mm) |
|---|---|
| 0.3 | 4 |
| 1 | 13 |
| 2 | 18 |
| 4 | 24 |
| 8 | 30 |

EXAMPLE 2

Whatman #1 paper was saturated with a solution of 1.5 g of o-tolidine in 10 cc of acetone and 90 cc of isopropanol, and air dried, giving a white detector paper. A 2.5 mm wide strip in a 5 mm ID dosimeter tube developed a 25 mm gray/green stain when exposed to an atmosphere containing 5 ppm $NO_2$ for 8 hours.

EXAMPLE 3

Whatman #1 paper was saturated with a solution of 0.025 g. phenolsulfonephthalein sodium salt and 0.1 g sodium carbonate in 75 cc deionized water, 30 cc isopropanol and 5 cc glycerine, and then air dried, giving a red-purple detector paper. A 2.5 mm wide strip in a 5 mm ID tube developed a 42 mm pale yellow stain when exposed to an atmosphere containing 5 pp $SO_2$ for 8 hours.

EXAMPLE 4

Whatman #1 paper was saturated with a solution of 1 g bromophenol blue in 50 cc deionized water and 50 cc isopropanol and then air dried, giving an orange detector paper. A 2.5 mm wide strip in a 5 mm ID tube developed a 28 mm blue stain when exposed to an atmosphere containing 25 ppm $NH_3$ for 8 hours.

EXAMPLE 5

Whatman 31 paper was saturated with a solution of 0.32 g Pb $(C_2H_3O_2)_2.3H_2O$ in 90 cc deionized water, 5 cc isopropanol and 5 cc glycerine, and then air dried, giving a white detector paper. A 2.5 mm wide strip in a 5 mm ID tube developed a 34 mm brownish-black stain when exposed to an atmosphere containing 10 ppm $H_2S$ for 8 hours.

We claim:

1. A colorimetric gas dosimeter comprising a transparent tube having closed ends, one of said ends being openable, a detecting strip of a substrate carrying a reagent that changes color on contact with the gas to be determined, the strip being disposed lengthwise in the tube with one end of the strip spaced from the openable end of the tube by a diffusion path and with at least one side of said strip spaced apart from said tube along a substantial portion of the length of said strip.

2. A dosimeter of claim 1 in which the reagent is impregnated in a porous substrate.

3. A dosimeter of claim 1 in which the reagent includes a humectant.

4. A dosimeter of claim 1 for determining hydrogen sulfide in which the reagent is silver cyanide.

5. A dosimeter of claim 1 for determining nitrogen dioxide in which the reagent is o-tolidine.

6. A dosimeter of claim 3 for determining hydrogen sulfide in which the reagent is lead acetate.

7. A dosimeter of claim 3 for determining sulfur dioxide in which the reagent is phenolsulfonephthalein sodium salt and sodium carbonate.

8. A dosimeter of claim 1 for determining ammonia in which the reagent is bromophenol blue.

9. A dosimeter of claim 1 in which the inside diameter of the tube is between about 2 and 6 millimeters.

10. A dosimeter of claim 1 in which the diffusion path comprises a plug of open cell foam.

11. A dosimeter of claim 1 in which the substrate is filter paper and the reagent includes a humectant.

12. A colorimetric gas dosimeter comprising a transparent tube having closed ends, one of said ends being openable, a detecting strip of a substrate carrying a reagent that changes color on contact with the gas to be determined, the strip being disposed lengthwise in the tube with one end of the strip spaced from the openable end of the tube by a diffusion path and with at least one side of said strip spaced apart from said tube along a substantial portion of the length of said strip, a resilient grommet having an axial aperture releasably engaging the end of the tube opposite the openable end, and a second transparent tube longer than the first tube and releasably engaging the outer surface of the grommet.

* * * * *